(12) United States Patent
Moser et al.

(10) Patent No.: US 12,221,446 B2
(45) Date of Patent: Feb. 11, 2025

(54) CRYSTALLINE SALT OF 5-METHYL-(6S)-TETRAHYDROFOLIC ACID AND L-ISOLEUCINE ETHYL ESTER

(71) Applicant: Merck Patent GmbH, Darmstadt (DE)

(72) Inventors: Rudolf Moser, Schaffhausen (CH); Viola Groehn, Dachsen (CH); Ruth Boehni Stamm, Stein Am Rhein (CH); Fritz Blatter, Reinach (CH); Martin Szelagiewicz, Basel (CH)

( * ) Notice: Subject to any disclaimer, the term of this patent is extended or adjusted under 35 U.S.C. 154(b) by 877 days.

(21) Appl. No.: 17/258,257

(22) PCT Filed: Jul. 2, 2019

(86) PCT No.: PCT/EP2019/067694
§ 371 (c)(1),
(2) Date: Jan. 6, 2021

(87) PCT Pub. No.: WO2020/007836
PCT Pub. Date: Jan. 9, 2020

(65) Prior Publication Data
US 2021/0269444 A1 Sep. 2, 2021

(30) Foreign Application Priority Data
Jul. 6, 2018 (EP) ..................... 18182278

(51) Int. Cl.
*C07D 475/04* (2006.01)
*C07C 229/08* (2006.01)

(52) U.S. Cl.
CPC .......... *C07D 475/04* (2013.01); *C07C 229/08* (2013.01); *C07B 2200/13* (2013.01)

(58) Field of Classification Search
CPC .................................................. C07D 475/04
See application file for complete search history.

(56) References Cited

U.S. PATENT DOCUMENTS

| 5,300,505 | A | 4/1994 | Muller et al. |
| 6,441,168 | B1* | 8/2002 | Muller .............. A61P 39/02 544/258 |
| 6,858,731 | B1 | 2/2005 | Muller et al. |
| 7,816,525 | B1 | 10/2010 | Muller et al. |
| 2021/0277006 | A1* | 9/2021 | Moser ................ A61K 45/06 |

FOREIGN PATENT DOCUMENTS

| CN | 1360586 A | 7/2002 |
| CN | 1360587 A | 7/2002 |
| CN | 106986873 A | 7/2017 |
| EP | 1044975 A1 | 10/2000 |
| JP | H05294968 A | 11/1993 |
| JP | 2011512366 A | 4/2011 |
| WO | 2009103334 A1 | 8/2009 |

OTHER PUBLICATIONS

Office Action in corresponding CN application No. 201980042510.3 dated Feb. 14, 2023 (pp. 1-10) and english translation thereof.
International Search Report dated Sep. 13, 2019 issued in corresponding PCT/EP2019/067694 application (3 pages).
Office Action in corresponding Japanese Patent Application No. 2021-500054 dated Jul. 11, 2023 (pp. 1-3).
China National Intellectual Property Administration: Board Opinion Jul. 18, 2024 in Application No. CN201980042510.6.
English Translation of China National Intellectual Property Administration: Board Opinion Jul. 18, 2024 in Application No. CN201980042510.6.
Food Molecular Biology (Second Edition), Ning Zhengxiang, China Light Industry Press, p. 10, Jul. 2014.
English Translation of Food Molecular Biology (Second Edition), Ning Zhengxiang, China Light Industry Press, p. 10, Jul. 2014.

\* cited by examiner

*Primary Examiner* — John S Kenyon
(74) *Attorney, Agent, or Firm* — Millen White Zelano & Branigan; Csaba Henter

(57) ABSTRACT

The present invention is directed to a crystalline salt of 5-methyl-(6S)-tetrahydrofolic acid and L-isoleucine ethyl ester wherein the molar ratio of 5-methyl-(6S)-tetrahydrofolic acid to L-isoleucine ethyl ester is from 1:0.3 to 1:2.0 (in mol/mol) and/or hydrates and/or solvates thereof, as well as, a process of obtaining the same.

26 Claims, 8 Drawing Sheets

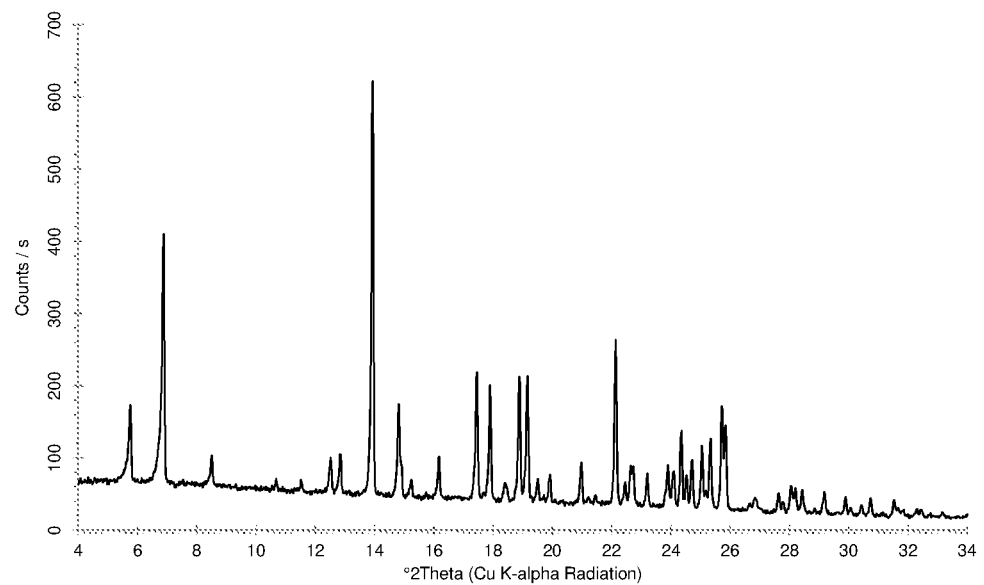
Figure 1: PXRD pattern of the salt of 5-methyl-(6S)-tetrahydrofolic acid and L-isoleucine ethyl ester (Form A).

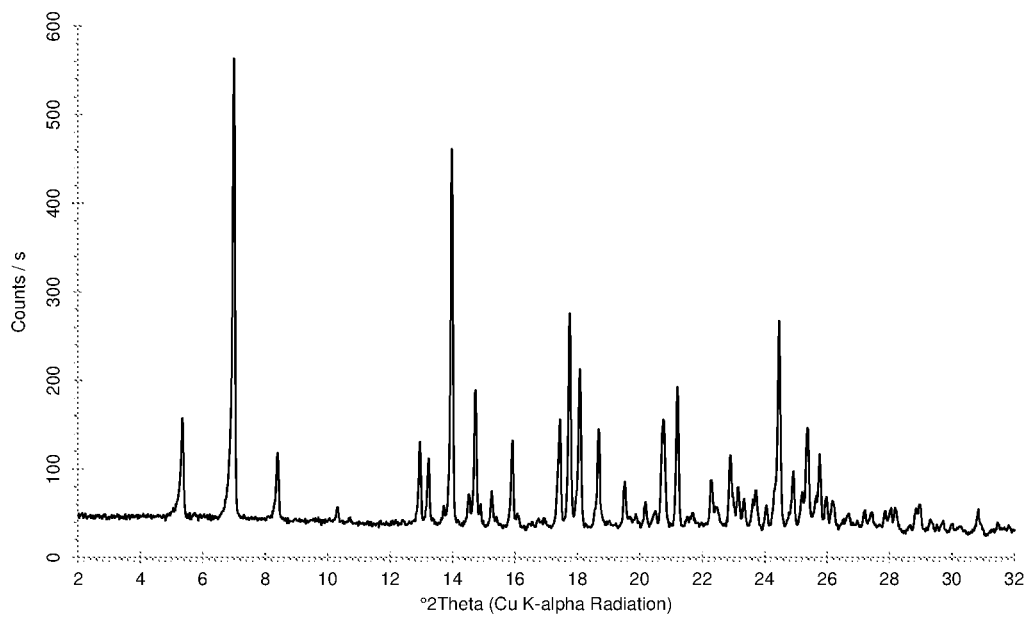
Figure 2: PXRD pattern of the salt of 5-methyl-(6S)-tetrahydrofolic acid and L-isoleucine ethyl ester (Form B).
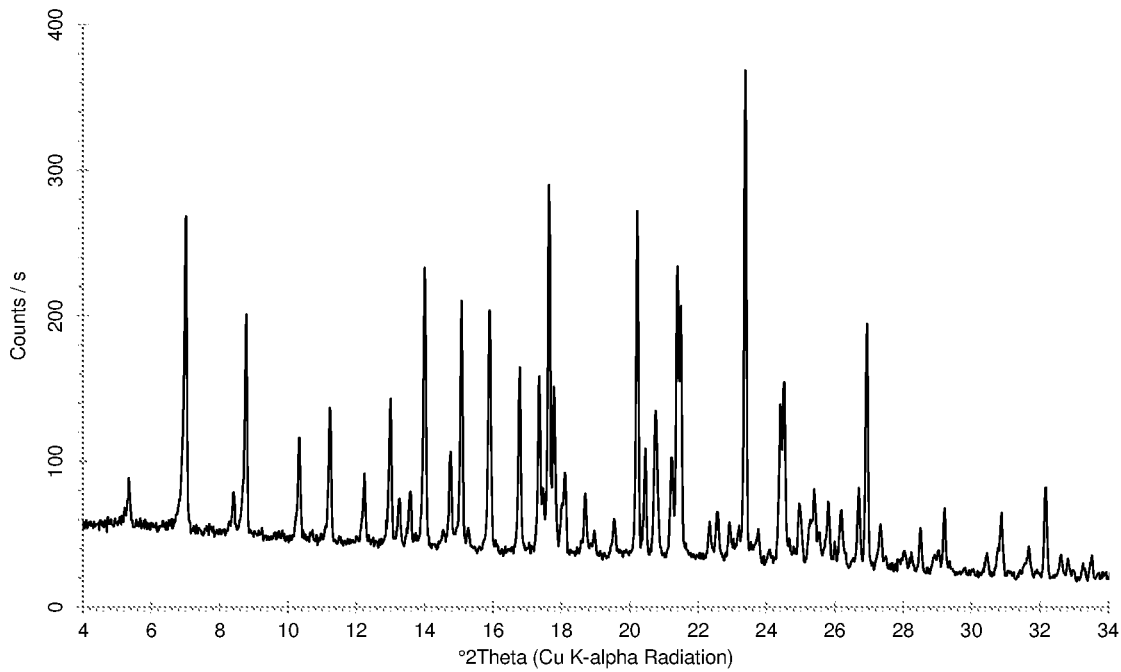
Figure 3: PXRD pattern of the salt of 5-methyl-(6S)-tetrahydrofolic acid and L-isoleucine ethyl ester (Form C).

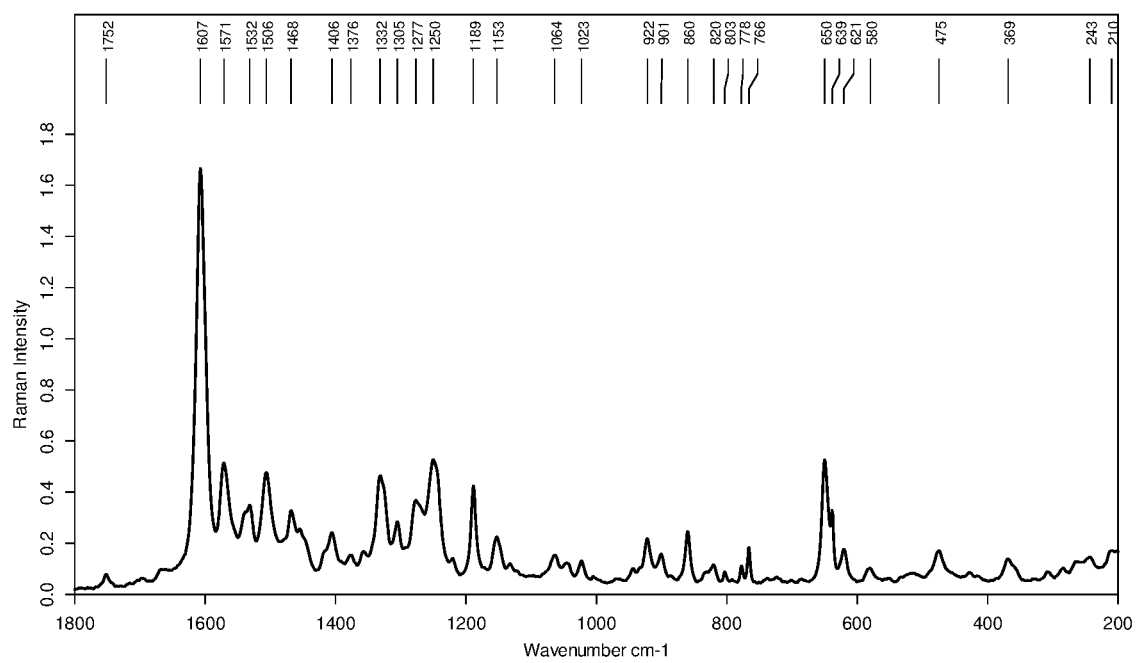
Figure 4: FT-Raman spectrum of the salt of 5-methyl-(6S)-tetrahydrofolic acid and L-isoleucine ethyl ester (Form A).

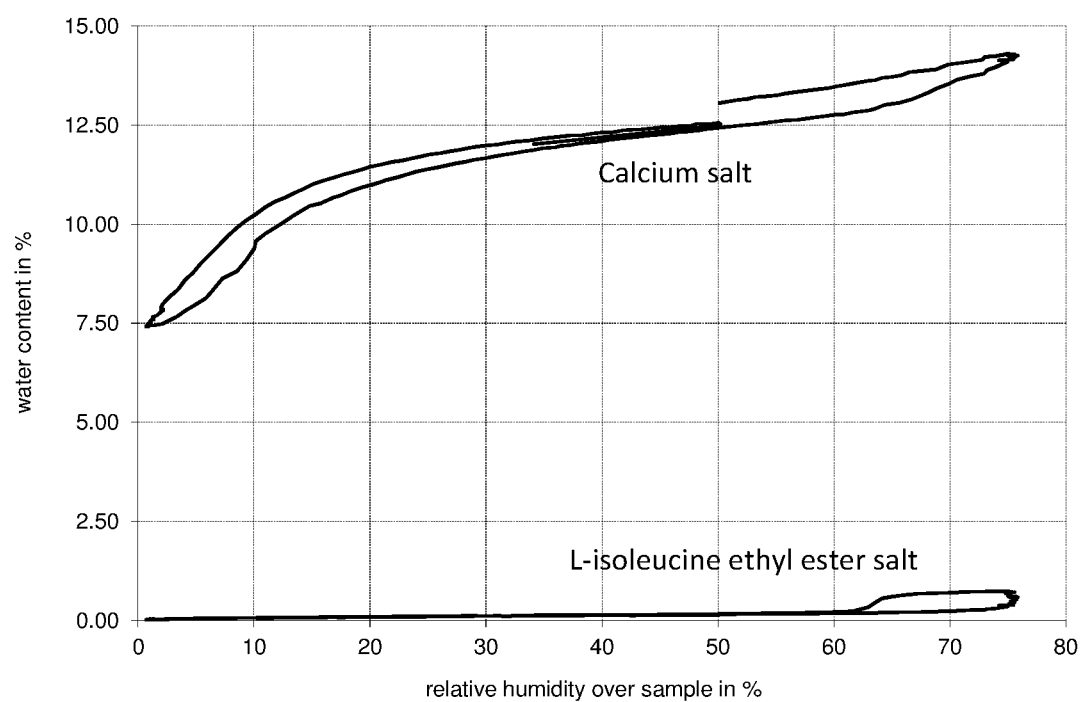
Figure 5: Dynamic water vapor sorption analysis of the calcium salt of 5-methyl-(6S)-tetrahydrofolic acid resp. the salt of 5-methyl-(6S)-tetrahydrofolic acid and L-isoleucine-ethyl ester (Form A).

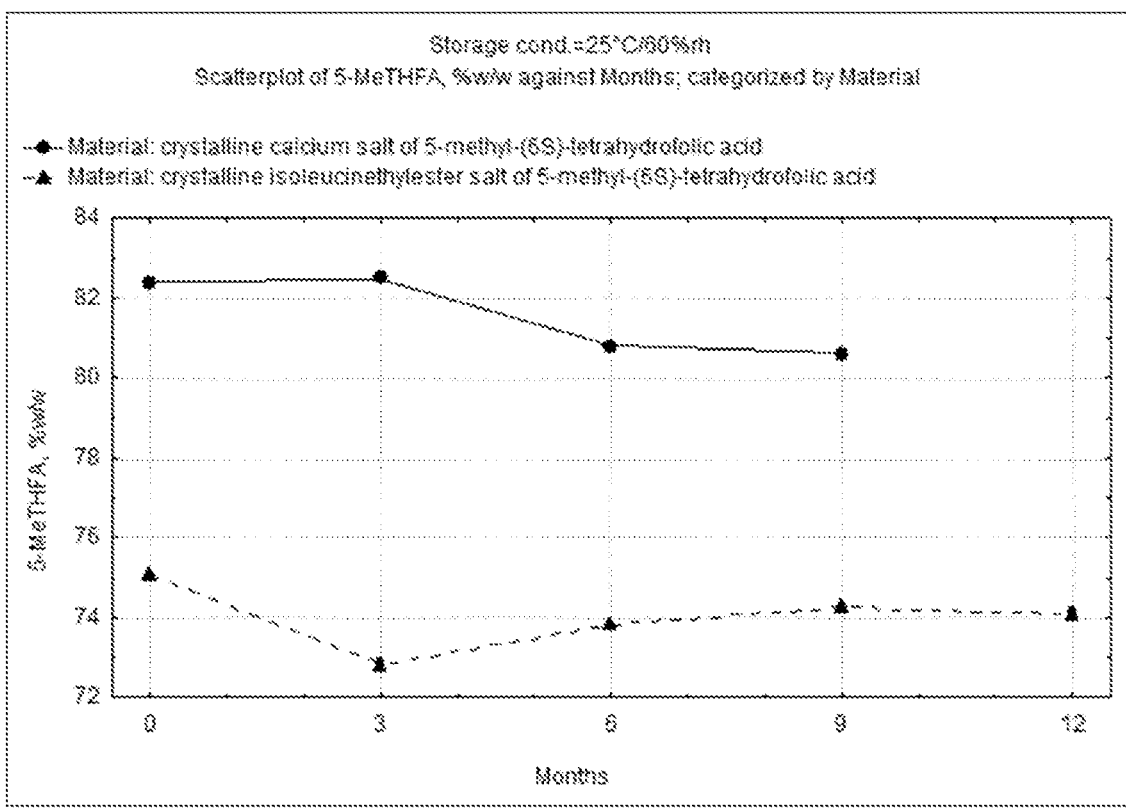
Figure 6: Long-term stability of the salt of 5-methyl-(6S)-tetrahydrofolic acid and L-isoleucine ethyl ester at 25°C/60%rh

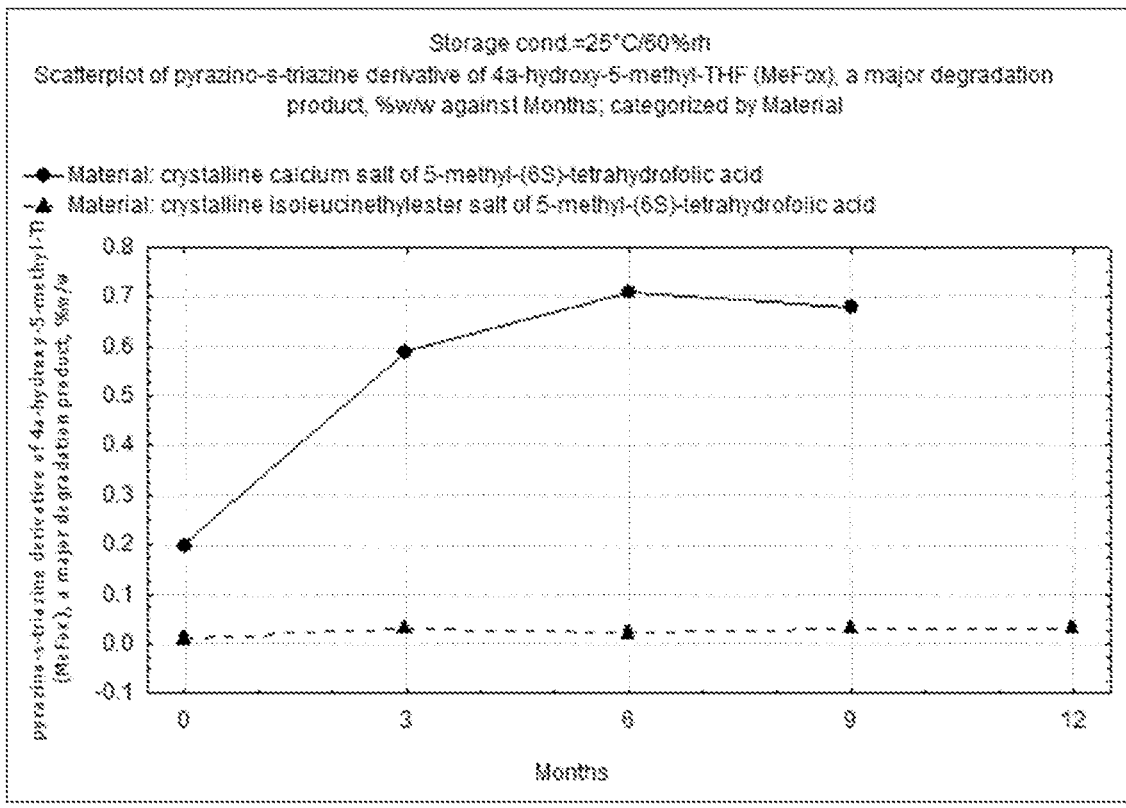
Figure 7: Long-term stability of the salt of 5-methyl-(6S)-tetrahydrofolic acid and L-isoleucine ethyl ester at 25°C/60%rh (major degradation product [MeFox])

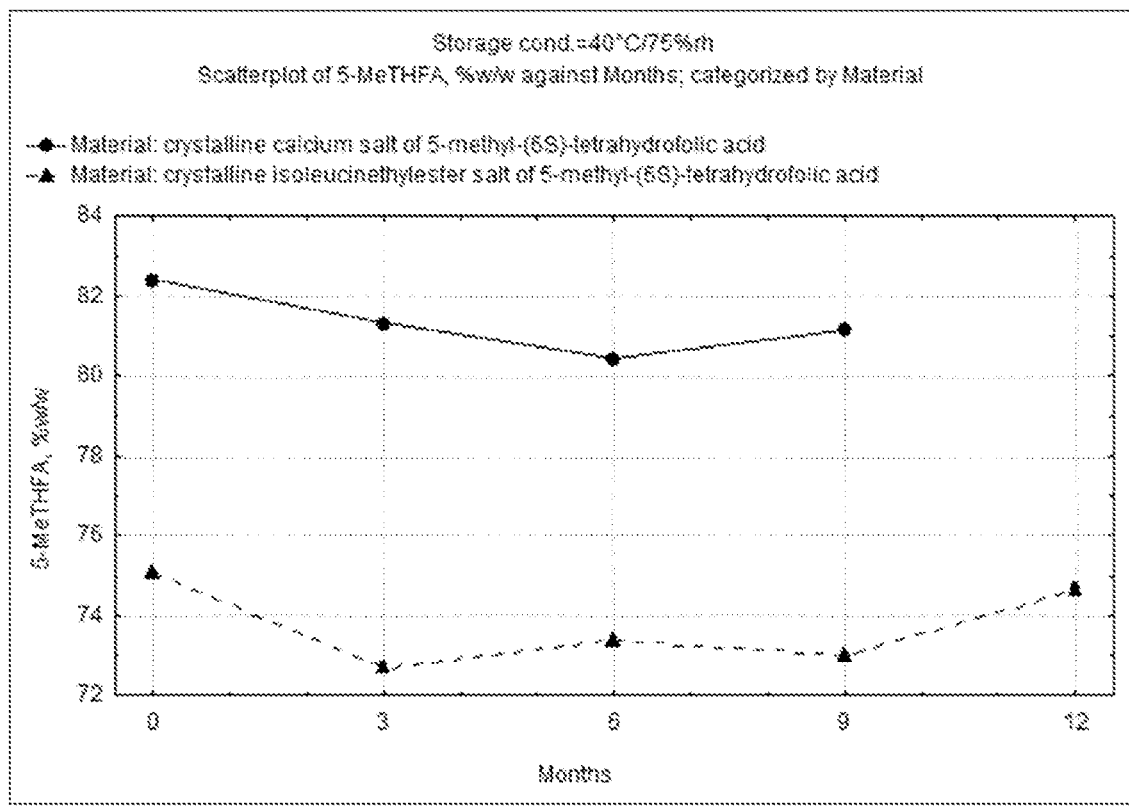
Figure 8: Long-term stability of the salt of 5-methyl-(6S)-tetrahydrofolic acid and L-isoleucine ethyl ester at 40°C/75%rh

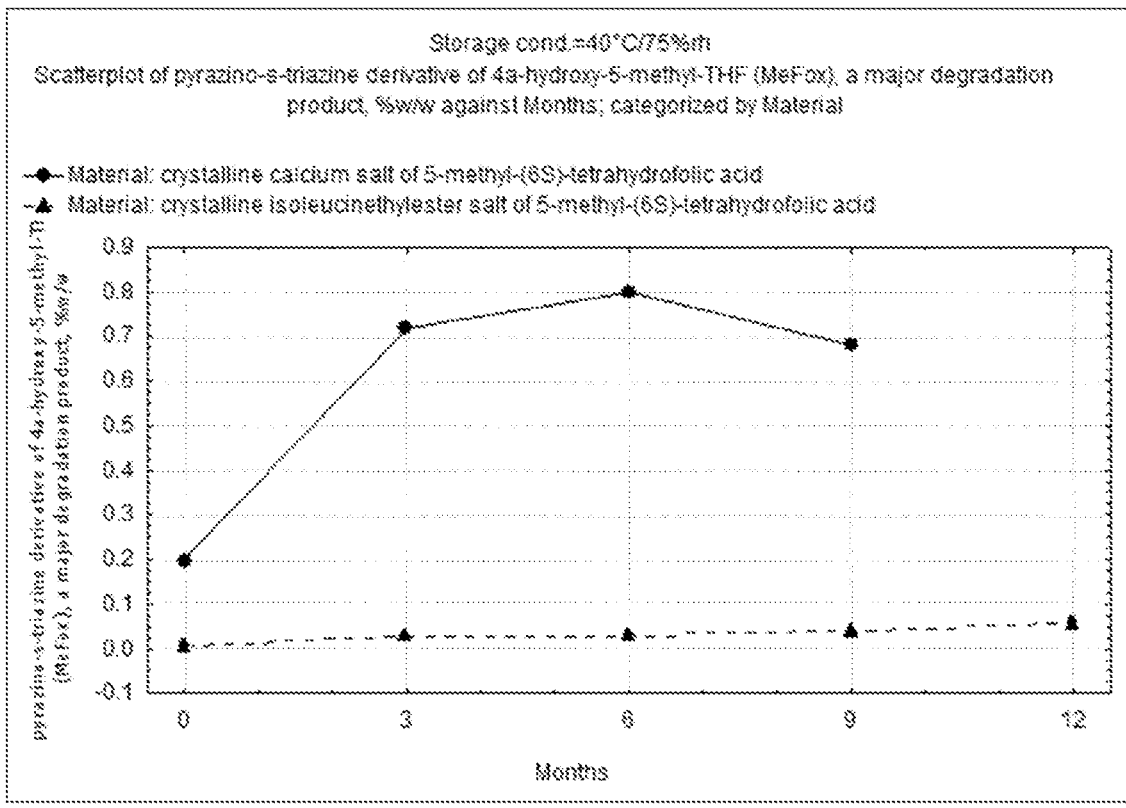
Figure 9: Long-term stability of the salt of 5-methyl-(6S)-tetrahydrofolic acid and L-isoleucine ethyl ester at 40°C/75%rh (major degradation product [MeFox])

CRYSTALLINE SALT OF 5-METHYL-(6S)-TETRAHYDROFOLIC ACID AND L-ISOLEUCINE ETHYL ESTER

The present invention is directed to a crystalline salt of 5-methyl-(6S)-tetrahydrofolic acid (N-[4-[[(2-amino-1,4,5,6,7,8-hexahydro-5-methyl-4-oxo-(6S)-pteridinyl)methyl]amino]benzoyl]-L-glutamic acid) and L-isoleucine ethyl ester and a process of obtaining the same.

Tetrahydrofolates are predominantly used as the calcium salt of 5-formyltetrahydrofolic acid (leucovorin and levoleucovorin), as the calcium salt of 5-methyltetrahydrofolic acid (Metafolin®), or as the sulfate salt of 5,10-methylenetetrahydrofolic acid (Modufolin®). Most prominent fields of use are for the treatment of megaloblastic folic acid anaemia, as an antidote for increasing the compatibility of folic acid antagonists, particularly of aminopterin and methotrexate in cancer therapy ("antifolate rescue"), for increasing the therapeutic effect of fluorinated pyrimidines and for the treatment of autoimmune diseases such as psoriasis and rheumatoid arthritis, for increasing the compatibility of certain antiparasitic for mutations, for instance trimethoprim-sulfamethoxazole, and for reducing the toxicity of dideazatetrahydrofolates in chemotherapy.

The calcium salt of 5-methyl-(6S)-tetrahydrofolic acid is used in particular as a drug and as a food additive, as a vitamin preparation, for the prevention of neural tube defects, for the treatment of depressive illnesses, and for influencing the homocysteine level. 5-Methyl-(6S)-tetrahydrofolic acid and salts thereof are known to be extremely unstable. In particular they are highly susceptible to oxidation [see also A. L. Fitzhugh, Pteridines 4 (4), 187-191 (1993) in this respect] and therefore difficult to produce at a level of purity which is acceptable for a pharmaceutical active ingredient or a food additive.

Various methods, such as excluding oxygen as completely as possible or the addition of antioxidants such as ascorbic acid or reduced L-glutathione, have been employed in order to overcome the instability of 5-methyltetrahydrofolic acid and salts thereof.

U.S. Pat. No. 6,441,168 B1 discloses alkaline earth metal salts of 5-methyltetrahydrofolic acid, particularly the calcium salt, its crystallization and its use. The drawback of such crystalline calcium salt of 5-methyl-(6S)-tetrahydrofolic acid is that it exists in its crystalline form in up to four polymorphic modifications. Therefore, the process of manufacturing the crystalline calcium salt of 5-methyl-(6S)-tetrahydrofolic acid has to be controlled very precisely. Additionally, the crystalline calcium salt of 5-methyl-(6S)-tetrahydrofolic acid of U.S. Pat. No. 6,441,168 B1 typically contains in the crystal lattice of all its polymorphic forms at least one but up to four equivalents of water per equivalent of 5-methyl-(6S)-tetrahydrofolic acid.

US 2016207925 A1 is claiming lyophilised, spray-dried or boiled down compositions comprising L-asparagine or L-arginine together with 5-methyl-(6S)-tetrahydrofolic acid. However, the disclosed compositions are simple, non-stochiometric mixtures and exist in an amorphous state.

New crystal forms of a pharmaceutically useful compound offer an opportunity to improve the performance profile of a pharmaceutical and/or vitamin/medical food products. It widens the reservoir of materials a formulation scientist has available for designing new dosage forms with improved characteristics.

The technical problem underlying the present invention is the provision of a crystalline form comprising 5-methyl-(6S)-tetrahydrofolic acid which overcomes the drawbacks of the crystalline calcium salt of 5-methyl-(6S)-tetrahydrofolic acid known in the art.

Additionally, new crystalline forms often show desired different physical and/or biological characteristics, which may assist in the manufacture or formulation of the active compound, to the purity levels and uniformity required for regulatory approval.

For the sake of stability of tetrahydrofolates it is always the aim to provide a compound which has a low water absorption upon storage and which can be dried sufficiently during manufacturing. In addition, drug substances that do not absorb high amounts of water under ambient conditions are highly desired. Particularly desired are substances that do not change their water content when the ambient relative humidity changes because large changes of the water content due to change of the relative humidity of the environment make it more difficult to achieve a great precision with the respect to the dosage form.

The technical problem is solved by a crystalline salt of 5-methyl-(6S)-tetrahydrofolic acid and L-isoleucine ethyl ester, wherein the molar ratio of 5-methyl-(6S)-tetrahydrofolic acid to L-isoleucine ethyl ester is from 1:0.3 to 1:2.0 (in mol/mol) and/or hydrates and/or solvates thereof.

The solid form of the present invention possesses improved pharmacological characteristics, thus offering enhanced possibilities to modulate and design improved drug products. Compared with the crystalline polymorphic forms of the calcium salt of 5-methyl-(6S)-tetrahydrofolic acid known in the art, the water adsorption of the crystalline salt of 5-methyl-(6S)-tetrahydrofolic acid and L-isoleucine ethyl ester is significantly lower leading to substantially improved control over the target dosage form level in the drug product because the change of the amounts of adsorbed water under changing relative humidity conditions is significantly less pronounced.

Another advantageous aspect of the crystalline salt of 5-methyl-(6S)-tetrahydrofolic acid and L-isoleucine ethyl ester is that a high chemical and optical purity of 5-methyl-(6S)-tetrahydrofolic acid can be achieved in one single crystallization step. So starting with tetrahydrofolic acid benzenesulfonate showing a diastereoisomerical purity of 95% one can end up in with a single crystallisation of the salt of 5-methyl-(6S)-tetrahydrofolic acid and L-isoleucine ethyl ester in a diastereoisomerical purity of more than 99%. On the other hand, when crystallising a calcium salt of 5-methyl-(6S)-tetrahydrofolic acid one need to have a starting material with a diastereoisomerical purity of at least 97.0% to end up with a final product showing a diastereoisomerical purity of more than 99%.

Typically, the crystalline salt of 5-methyl-(6S)-tetrahydrofolic acid and L-isoleucine ethyl ester has a molar ratio of 5-methyl-(6S)-tetrahydrofolic acid to L-isoleucine ethyl ester from 1:0.3 to 1:2.0 (in mol/mol).

Preferably, the crystalline salt has a molar ratio of 5-methyl-(6S)-tetrahydrofolic acid to L-isoleucine ethyl ester from 1:0.5 to 1:1.5 (in mol/mol).

Even more preferably, the crystalline salt has a molar ratio of 5-methyl-(6S)-tetrahydrofolic acid to L-isoleucine ethyl ester from 1:0.75 to 1:1.5 (in mol/mol).

In a further preferred embodiment, the molar ratio of 5-methyl-(6S)-tetrahydrofolic acid to L-isoleucine ethyl ester is from 1:0.75 to 1:1.25 (in mol/mol).

Most preferred, the ratio of 5-methyl-(6S)-tetrahydrofolic acid to L-isoleucine ethyl ester is approximately 1:1 (in mol/mol).

Preferably, the salt is the crystalline salt of 5-methyl-(6S)-tetrahydrofolic acid and L-isoleucine ethyl ester and has a PXRD pattern with at least one characteristic peak (expressed in 2θ±0.2° 2θ (CuKα radiation)) selected from the following peaks located at 5.8, 6.9, 14.0, 17.5, and 22.2, hereinafter designated as (Form A).

More preferred, the salt is the crystalline salt of 5-methyl-(6S)-tetrahydrofolic acid and L-isoleucine ethyl ester and has a PXRD pattern with at least three characteristic peaks (expressed in 2θ±0.2° 2θ (CuKα radiation)) selected from the following peaks located at 5.8, 6.9, 14.0, 17.5, and 22.2 (Form A). Even more preferred, the salt is the crystalline salt of 5-methyl-(6S)-tetrahydrofolic acid and L-isoleucine ethyl ester and has a PXRD pattern with peaks (expressed in 2θ±0.2° 2θ (CuKα radiation)) at 5.8, 6.9, 14.0, 17.5, and 22.2 (Form A).

Even more preferred, the salt is the crystalline salt of 5-methyl-(6S)-tetrahydrofolic acid and L-isoleucine ethyl ester and has a PXRD pattern with at least one characteristic peak (expressed in 2θ±0.2° 2θ (CuKα radiation)) selected from the following peaks located at 5.8, 6.9, 8.5, 12.5, 12.9, 14.0, 14.9, 16.2, 17.5, 17.9, 18.9, 19.2, 22.2, 24.4, 25.4 25.8, 25.9, and 34.6 (Form A).

Most preferred, the salt is the crystalline salt of 5-methyl-(6S)-tetrahydrofolic acid and L-isoleucine ethyl ester and has a PXRD pattern substantially as shown in FIG. 1 (Form A).

The salt of 5-methyl-(6S)-tetrahydrofolic acid and L-isoleucine ethyl ester can alternatively be characterized by Raman spectroscopy and thereby preferably the salt is the crystalline salt of 5-methyl-(6S)-tetrahydrofolic acid and L-isoleucine ethyl ester and has a Raman spectrum with at least one characteristic peak (expressed in wavenumbers, $cm^{-1} \pm 2\ cm^{-1}$) selected from the following peaks located at 1607, 1571, 1506, 1250, and 650 (Form A).

More preferred, the salt is the crystalline salt of 5-methyl-(6S)-tetrahydrofolic acid and L-isoleucine ethyl ester and has a Raman spectrum with at least three characteristic peaks (expressed in wavenumbers, $cm^{-1} \pm 2\ cm^{-1}$) selected from the following peaks located at 1607, 1571, 1506, 1250, and 650 (Form A). Even more preferred, the salt is the crystalline salt of 5-methyl-(6S)-tetrahydrofolic acid and L-isoleucine ethyl ester has a Raman spectrum with peaks (expressed in wavenumbers, $cm^{-1} \pm 2\ cm^{-1}$) at 1607, 1571, 1506, 1250, and 650 (Form A).

Even more preferred, the salt is the crystalline salt of 5-methyl-(6S)-tetrahydrofolic acid and L-isoleucine ethyl ester and has a Raman spectrum—with at least one characteristic peak (expressed in wavenumbers, $cm^{-1} \pm 2\ cm^{-1}$) selected from the following peaks located at 2961, 2938, 1607, 1571, 1506, 1468, 1332, 1250, 1153, 922, 860, and 650 (Form A).

Most preferred, the salt is the crystalline salt of 5-methyl-(6S)-tetrahydrofolic acid and L-isoleucine ethyl ester and has a Raman spectrum substantially as shown in FIG. 4 (Form A).

A further aspect of the present invention is the crystalline salt of 5-methyl-(6S)-tetrahydrofolic acid and L-isoleucine ethyl ester having a PXRD pattern with at least one characteristic peak (expressed in 2θ±0.2° 2θ (CuKα radiation)) selected from the following peaks located at 5.3, 7.0, 14.0, 17.7, and 24.5, hereinafter designated as Form B.

More preferred, the salt is the crystalline salt of 5-methyl-(6S)-tetrahydrofolic acid and L-isoleucine ethyl ester and has a PXRD pattern with at least three characteristic peaks (expressed in 2θ±0.2° 2θ (CuKα radiation)) selected from the following peaks located at 5.3, 7.0, 14.0, 17.7, and 24.5 (Form B). Even more preferred, the salt is the crystalline salt of 5-methyl-(6S)-tetrahydrofolic acid and L-isoleucine ethyl ester and has a PXRD pattern with peaks (expressed in 2θ±0.2° 2θ (CuKα radiation)) at 5.3, 7.0, 14.0, 17.7, and 24.5 (Form B)

Even more preferred, the salt is the crystalline salt of 5-methyl-(6S)-tetrahydrofolic acid and L-isoleucine ethyl ester has a PXRD pattern with at least one characteristic peak (expressed in 2θ±0.2° 2θ (CuKα radiation)) selected from the following peaks located at 5.3, 7.0, 8.4, 13.0, 13.2, 14.0, 14.7, 15.9, 17.4, 17.7, 18.1, 18.7, 20.7, 21.2, 22.9, 24.5, and 25.4 (Form B).

Most preferred, the salt is the crystalline salt of 5-methyl-(6S)-tetrahydrofolic acid and L-isoleucine ethyl ester and has a PXRD pattern substantially as shown in FIG. 2 (Form B).

While Form A is suitable for tablet formulations, Form B is stable in aqueous environments and thus well suited for ointment, suspensions or cream formulations that exhibit a high water activity.

A further aspect of the present invention is the crystalline salt of 5-methyl-(6S)-tetrahydrofolic acid and L-isoleucine ethyl ester having a PXRD pattern with at least one characteristic peak (expressed in 2θ±0.2° 2θ (CuKα radiation)) selected from the following peaks located at 7.0, 8.8, 14.0, 17.6, 20.2, 23.4, and 26.9, hereinafter designated as Form C.

More preferred, the salt is the crystalline salt of 5-methyl-(6S)-tetrahydrofolic acid and L-isoleucine ethyl ester and has a PXRD pattern with at least three characteristic peaks (expressed in 2θ±0.2° 2θ (CuKα radiation)) selected from the following peaks located at 7.0, 8.8, 14.0, 17.6, 20.2, 23.4, and 26.9 (Form C). Even more preferred, the salt is the crystalline salt of 5-methyl-(6S)-tetrahydrofolic acid and L-isoleucine ethyl ester and has a PXRD pattern with characteristic peaks (expressed in 2θ±0.2° 2θ (CuKα radiation)) at 7.0, 8.8, 14.0, 17.6, 20.2, 23.4, and 26.9 (Form C).

Even more preferred, the salt is the crystalline salt of 5-methyl-(6S)-tetrahydrofolic acid and L-isoleucine ethyl ester has a PXRD pattern with at least one characteristic peak (expressed in 2θ±0.2° 2θ (CuKα radiation)) selected from the following peaks located at 5.3, 7.0, 8.8, 11.2, 13.0, 14.0, 15.1, 15.9, 16.8, 17.4, 17.6, 20.2, 20.5, 20.8, 21.2, 21.4, 23.4, 24.5, 26.9, and 32.2 (Form C).

Most preferred, the salt is the crystalline salt of 5-methyl-(6S)-tetrahydrofolic acid and L-isoleucine ethyl ester and has a PXRD pattern substantially as shown in FIG. 3 (Form C).

Even more preferred, the aforementioned crystalline salts have at least 99 wt % or more chemical and/or stereoisomerical purity.

It is also advantageous having a form comprising 5-methyl-(6S)-tetrahydrofolic with a very low water content and especially a low tendency to absorb/desorb water, e.g. when handling the substance for compounding in a temperature/humidity controlled environment or in tropical countries, where the relative humidity generally is very high. The salt of 5-methyl-(6S)-tetrahydrofolic acid and L-isoleucine ethyl ester is showing generally a water content of below 1% whereas the calcium salt of 5-methyl-(6S)-tetrahydrofolic acid generally is having a water content of more than 10%. The results are visually illustrated in Example 9 resp. FIG. 5.

Additionally, beside of the very low water content of the salt of 5-methyl-(6S)-tetrahydrofolic acid and L-isoleucine ethyl ester this salt is also surprisingly showing an especially low tendency to absorb/desorb water over a broad range of humidity. So when comparing the water content of the salt of 5-methyl-(6S)-tetrahydrofolic acid and L-isoleucine ethyl ester (Form A) with the water content of the calcium salt of 5-methyl-(6S)-tetrahydrofolic over the most relevant range of relative humidity from 20 to 75% r.h., the water content of the salt of 5-methyl-(6S)-tetrahydrofolic acid and L-isoleucine ethyl ester (Form A) changes by less than 0.8%, Contrary thereto, the water content for the calcium salt of 5-methyl-(6S)-tetrahydrofolic acid according to the state of the art changes by more than 6%. The results are visually illustrated in Example 9, resp. FIG. 5. This result is very surprising to a person skilled in the art and could not be expected when considering the teaching of U.S. Pat. No. 6,441,168 B1. Moreover, the forms of the present invention clearly solve the technical problem underlying the present invention.

Additionally, the salt of 5-methyl-(6S)-tetrahydrofolic acid and L-isoleucine ethyl ester is showing a far better stability than the previously known calcium salt. So the salt of 5-methyl-(6S)-tetrahydrofolic acid and L-isoleucine ethyl ester is still showing a relative content of 5-methyl-(6S)-tetrahydrofolic acid (measured to the initial content at the start) of more than 98% w/w when stored over 12 months at 25° C./60% rh whereas the relative content of 5-methyl-(6S)-tetrahydrofolic acid of the calcium salt of 5-methyl-(6S)-tetrahydrofolic acid is decreasing to below 98% w/w already before reaching 9 months. The results are visually illustrated in Example 10 (Table 4b) resp. FIG. 6. In parallel the content of the major degradation product pyrazino-s-triazine derivative of 4α-hydroxy-5-methyl-THF [MeFox] is at a level of below 0.05% when stored over 12 months at 25° C./60% rh whereas the content of MeFox for the calcium salt of 5-methyl-(6S)-tetrahydrofolic acid has increased to over 0.6% already before reaching 9 months. The results are visually illustrated in Example 10, (Table 5) resp. FIG. 7.

The surprisingly high stability of the salt of 5-methyl-(6S)-tetrahydrofolic acid and L-isoleucine ethyl ester is even more particularly emphasised when comparing stability values at 40° C./75% rh. Even under these elevated conditions the salt of 5-methyl-(6S)-tetrahydrofolic acid and L-isoleucine ethyl ester is still showing a relative content of 5-methyl-(6S)-tetrahydrofolic acid (measured to the initial content at the start) of more than 99% when stored over 12 months whereas the relative content of 5-methyl-(6S)-tetrahydrofolic acid of the calcium salt of 5-methyl-(6S)-tetrahydrofolic acid is decreasing to below 99% already before reaching 9 months when stored at the same conditions. The results are visually illustrated in Example 10 (Table 6b) resp. FIG. 8. In parallel the content of the major degradation product pyrazino-s-triazine derivative of 4α-hydroxy-5-methyl-THF [MeFox] is just at a level of 0.06% when stored over 12 months at 25° C./60% rh whereas the content of MeFox for the calcium salt of 5-methyl-(6S)-tetrahydrofolic acid has increased to over 0.6% already before reaching 9 months. The results are visually illustrated in Example 10, (Table 7) resp. FIG. 9.

Thus, the form of the present invention exhibits improved storage stability even under these conditions. These improved properties were not derivable bearing the teaching of U.S. Pat. No. 6,441,168 B1 in mind.

A further aspect of the present invention is a process for obtaining the crystalline salt of 5-methyl-(6S)-tetrahydrofolic acid and L-isoleucine ethyl ester comprising the steps of:
i) preparing a mixture of 5-methyl-(6S)-tetrahydrofolic acid in water and adding L-isoleucine ethyl ester, optionally in a suitable solvent or a mixture of solvents;
ii) adding a base, optionally in a suitable solvent or a mixture of solvents to achieve dissolution;
iii) heating the composition to at least 60° C.;
iv) adding a suitable acid to adjust the pH to the range from 4 to 7;
v) crystallizing and cooling the mixture to a temperature between 1° C. and 30° C., optionally stirring the obtained suspension at the end temperature; and
vi) isolating the obtained solid material and optionally drying the product.

The crystalline salt of 5-methyl-(6S)-tetrahydrofolic acid and L-isoleucine ethyl ester can surprisingly be obtained according to the disclosed process highly efficiently and in a high chemical, stereoisomerical and crystalline purity, even when prepared from 5-methyl-(6S)-tetrahydrofolic acid with 95.0% optical purity, that was in situ formed from (6S)-tetrahydrofolic acid benzenesulfonate with an optical purity of only 95.0% of (6S)-tetrahydrofolic acid. So when starting with an optical purity of the (6S)-tetrahydrofolic acid benzenesulfonate of 95.0% one is ending up with an optical purity of the crystalline salt of 5-methyl-(6S)-tetrahydrofolic acid and L-isoleucine ethyl ester of more than 99%. Generally crystalline salt of 5-methyl-(6S)-tetrahydrofolic acid and L-isoleucine ethyl ester prepared according to the disclosed process have an optical purity of more than 99%, preferably of more than 99.5% and a chemical purity of more than 98%, preferably more than 99%, even more preferred more than 99.5%.

Preferably in step i) the mixture of 5-methyl-(6S)-tetrahydrofolic acid in water is prepared in situ from (6S)-tetrahydrofolic acid benzenesulfonic acid (prepared according to EP 0 495 204 B1) which is subjected to a reductive methylation by using formaldehyde and sodium borohydride in an inert atmosphere.

Preferably in step i) L-isoleucine ethyl ester is added in form of its hydrochloride salt.

Preferably, the molar ratio of 5-methyl-(6S)-tetrahydrofolic acid and L-isoleucine ethyl ester hydrochloride in step i) is in the range of from 1:1 to 1:3.

Preferably, in step ii) the base used to enable dissolution of 5-methyl-(6S)-tetrahydrofolic acid is an alkali metal hydroxide. More preferably in step ii) the base is NaOH, KOH and/or mixtures thereof. Most preferred in step ii) the base is aqueous sodium hydroxide solution.

Even more preferred, in step ii) or step iii) the pH after the addition of the base is in the range of from 6.5 to 9.0.

Most preferred, the solvent used in step i) and/or step ii) is water.

Optionally in step iii) charcoal is added and then the solution is clear filtrated.

Preferably, in step iv) aqueous hydrochloric acid is used as a suitable acid.

More preferred, in step iv) the pH value achieved by addition of the acid is set to be in the range of from 4.4 to 6.4. Most preferred, in step iv) the pH is in the range from 5.4 to 6 after addition of the acid.

In step iii), iv) and/or v) seed crystals may be added, being even more preferred seed crystals of the desired form.

A further aspect of the present invention is a pharmaceutical composition, food additive and/or preparation comprising the salt of 5-methyl-(6S)-tetrahydrofolic acid and L-isoleucine ethyl ester and optionally one or more acceptable excipients.

The salt of 5-methyl-(6S)-tetrahydrofolic acid and L-isoleucine ethyl ester can be used as constituent for the production of drugs and/or as a food additive.

The salt of 5-methyl-(6S)-tetrahydrofolic acid and L-isoleucine ethyl ester can be used in the treatment of anemia, neural tube defects (NTDs), cardiovascular diseases (CVD), depression, Alzheimer's disease and osteoporosis and/or dietary management of low plasma and/or low red blood cell folate (medical food).

Pharmaceutical compositions according to the present invention can be applied for all modes of administration, preferably for oral, parenteral, intramuscular, intraspinal, intrathecal, periodontal, topical or rectal administration.

In summary, the profile of properties offered by the salt of 5-methyl-(6S)-tetrahydrofolic acid and L-isoleucine ethyl ester of the present invention is advantageous for use in medicaments or as food additive. Especially, the enhanced stability, the low change in water content in an environment from 20% to 75% relative humidity and the increased optical purification when crystallising the salt of 5-methyl-(6S)-tetrahydrofolic acid and L-isoleucine ethyl ester could not been foreseen by the skilled artisan.

EXAMPLES

Powder X-Ray Diffraction

Stoe Stadi P equipped with a Mythen1 K Detector; Cu-Kα1 radiation; standard measurement conditions: transmission; 40 kV and 40 mA tube power; curved Ge monochromator; 0.02° 2θ step size, 48 s step time, 1.5-50.5° 2θ scanning range; detector mode: step scan; 1° 2θ detector step; standard sample preparation: 10 to 20 mg sample was placed between two acetate foils; sample holder: Stoe transmission sample holder; the sample was rotated during the measurement. All sample preparation and measurement was done in an ambient air atmosphere.

TG-FTIR

Thermogravimetric measurements were carried out with a Netzsch Thermo-Microbalance TG 209 coupled to a Bruker FTIR Spectrometer Vector 22 (sample pans with a pinhole, $N_2$ atmosphere, heating rate 10 K/min).

DVS

DVS measurements are typically performed with an SPS11-100n "Sorptions Prüfsystem" from ProUmid (formerly "Projekt Messtechnik"), August-Nagel-Str. 23, 89079 Ulm (Germany).

Raman Spectroscopy

FT-Raman spectra were recorded on a Bruker MultiRAM FT-Raman or a Bruker RFS 100 FT-Raman system with a near infrared Nd:YAG laser operating at 1064 nm and a liquid nitrogen-cooled germanium detector. 64 scans with a resolution of 2 cm$^{-1}$ were accumulated in the range from 3500 to −50 cm$^{-1}$; however, only data above 100 cm$^{-1}$ are evaluated due to filter cutoff effects. Nominal laser powers are typically 100 or 300 mW.

Example 1: Preparation of the Salt of 5-methyl-(6S)-tetrahydrofolic acid and L-isoleucine ethyl ester Form A without Seeding A suspension of 2.00 grams of 5-methyl-(6S)-tetrahydrofolic acid (assay: 95.6% w/w) in 20.0 ml water was heated to 70° C. and 2.13 grams of L-isoleucine ethyl ester hydrochloride is added. The temperature in the suspension was 65° C. and sodium hydroxide was added in form of a 30% (w/w) concentrated aqueous solution. In total, 0.95 g of the 30% sodium hydroxide solution were added. Addition of sodium hydroxide leaded to an essentially clear solution that gradually changed into a concentrated suspension. The suspension was diluted with 20.0 ml of water and the heater was switched off to allow the mixture to cool to ambient temperature within about two hours. The reactor with the suspension was further cooled in an ice/water bath to about 10° C. within half an hour, then filtered with a fritted glass filter and washed with five ml of cold water. The solid product was dried in a vacuum dryer at 35° C. for about 20 hours and examined by powder X-ray diffraction and identified as 5-methyl-(6S)-tetrahydrofolic acid L-isoleucine ethyl ester salt Form A. The powder X-ray diffraction pattern of Form A is depicted in FIG. 1 and exhibits peaks at 2-theta angles as listed in Table 1. HPLC analysis showed that the purity is 98.65% area.

TABLE 1

2-theta angles, d-spacings and qualitative intensities for Form A.

| angle °2Θ | d-spacing [Å] | qualitative intensity |
|---|---|---|
| 5.8 | 15.34 | m |
| 6.9 | 12.81 | vs |
| 8.5 | 10.39 | w |
| 10.7 | 8.27 | w |
| 11.6 | 7.64 | w |
| 12.5 | 7.05 | m |
| 12.9 | 6.88 | m |
| 14.0 | 6.34 | vs |
| 14.9 | 5.96 | m |
| 15.3 | 5.80 | w |
| 15.8 | 5.62 | w |
| 16.2 | 5.47 | w |
| 17.5 | 5.07 | s |
| 17.9 | 4.94 | m |
| 18.4 | 4.81 | w |
| 18.9 | 4.69 | m |
| 19.2 | 4.62 | m |
| 19.5 | 4.54 | w |
| 19.9 | 4.45 | w |
| 21.0 | 4.23 | w |
| 21.5 | 4.14 | vw |
| 22.2 | 4.01 | m |
| 22.5 | 3.95 | w |
| 22.7 | 3.91 | w |
| 23.2 | 3.83 | w |
| 23.9 | 3.72 | w |
| 24.1 | 3.68 | w |
| 24.4 | 3.65 | m |
| 24.7 | 3.60 | w |
| 25.1 | 3.55 | w |
| 25.4 | 3.51 | m |
| 25.8 | 3.45 | m |
| 26.9 | 3.31 | vw |
| 27.7 | 3.22 | w |
| 28.2 | 3.16 | w |
| 28.5 | 3.13 | w |
| 28.9 | 3.09 | vw |
| 29.2 | 3.06 | w |
| 29.7 | 3.01 | vw |
| 29.9 | 2.98 | w |
| 30.5 | 2.93 | vw |

Vs = very strong, s = strong, m = medium, w = weak, and vw = very weak in intensity. It should be noted that intensity values can vary substantially due to preferred orientation effects.

Example 2: Preparation of the Salt of 5-methyl-(6S)-tetrahydrofolic acid and L-isoleucine ethyl ester Form A with Seeding To 15 g of 5-methyl-(6S)-tetrahydrofolic acid (assay: 95.4% w/w, 6S-diastereoisomer: 97.74%) were added 225 g water under a nitrogen atmosphere. The pH was adjusted to 6.5 by addition of aqueous sodium hydroxide solution (30% w/w). The mixture was heated to 66° C. and further aqueous sodium hydroxide solution (30% w/w) was added to keep the pH at 6.5. A solution of 15.2 g L-isoleucine ethyl ester hydrochloride in 75 g water was added at 66° C. After seeding with 5-methyl-(6S)-tetrahydrofolic acid L-isoleucine ethyl ester salt Form A at 66° C. the mixture was stirred for 16 hours at 66° C. The mixture was cooled to 1° C. while the pH was adjusted to 5.7 by addition of aqueous 1 molar hydrochloric acid. After stirring for 1 hour at 1° C. the crystalline material was isolated by suction filtration and washed with 44 g water that was pre-cooled to 1° C. The material was dried at 36° C. in vacuum for 22 hours to give 14.6 g of 5-methyl-(6S)-tetrahydrofolic acid L-isoleucine ethyl ester salt corresponding to 75% of theoretical yield (assay corrected). (Analytical data of isolated product: purity: 98.9% area, assay: 73.95% w/w 5-methyl-(6S)-tetrahydrofolic acid corresponding to the 1:1 salt, loss on drying (residual water): 1.2% w/w, (6S)-diastereoisomer: 99.8%. TG-FTIR analysis showed that the obtained solid product is essentially free of water as the mass loss at 150° C. is not more than about 0.2%. H-NMR spectroscopic analysis shows that the molar ratio of 5-methyl-(6S)-tetrahydrofolic acid to L-isoleucine ethyl ester is about 1:1. The powder X-ray diffraction pattern as shown in FIG. 1 corresponds to Form A.

Example 3: Preparation of the Salt of 5-methyl-(6S)-tetrahydrofolic acid an L-isoleucine ethyl ester Salt Form A 1.92 g of 5-methyl-(6S)-tetrahydrofolic acid (4 mmol) were dissolved in 8.0 ml 1 N NaOH. The solution was heated to 80° C. 1.28 g L-isoleucine ethyl ester hydrochloride (~6.5 mmol) were dissolved in 6.0 ml water and added to the solution with the 5-methyl-(6S)-tetrahydrofolic acid. The solution was cooled to 60° C. within about 15 minutes and seeded with about 10 to 20 mg of 5-methyl-(6S)-tetrahydrofolic acid L-isoleucine ethyl ester salt Form A obtained according to Example 1. A test of the pH typically showed a pH of 7, then 2.0 ml of 1 N HCl were added dropwise. A suspension formed and the mixture was cooled to 5° C. at a rate of 15 degrees C. per hour. After about 30 minutes stirring at 5° C., the suspension was filtered and the solid product dried 24 hours under vacuum at 40° C. Powder X-ray diffraction of the sample showed that 5-methyl-(6S)-tetrahydrofolic acid L-isoleucine ethyl ester salt Form A was obtained.

Example 4: Preparation of the Salt of 5-methyl-(6S)-tetrahydrofolic acid and L-isoleucine ethyl ester Form B To a mixture of 6.0 ml water and 452 mg of 5-methyl-(6S)-tetrahydrofolic acid L-isoleucine ethyl ester salt Form A were added 6.0 ml of a 0.5 M solution of L-isoleucine ethyl ester hydrochloride in water and 2.0 ml ethanol at r.t. The pH was adjusted to pH~6-7 by addition of 0.250 ml 1 N NaOH and then the mixture was heated to 75° C. The temperature of the slightly yellow suspension was kept at 75° C. for 30 minutes. Then the mixture was allowed to cool to 25° C. within about three hours. Stirring at 25° C. was continued during about 4 hours and a solid sample, termed PP555-P40a, was recovered by centrifugal filtration and examined by PXRD without drying. The solid product was identified as 5-methyl-(6S)-tetrahydrofolic acid L-isoleucine ethyl ester salt Form B.

TABLE 2

2-theta angles, d-spacings and qualitative intensities for Form B.

| angle °2Θ | d-spacing [Å] | qualitative intensity |
|---|---|---|
| 5.3 | 16.6 | m |
| 7.0 | 12.6 | vs |
| 8.4 | 10.5 | m |
| 10.3 | 8.6 | w |
| 13.0 | 6.8 | m |
| 13.2 | 6.7 | m |
| 14.0 | 6.3 | vs |
| 14.5 | 6.1 | w |
| 14.7 | 6.0 | s |
| 15.3 | 5.80 | w |
| 15.9 | 5.56 | m |
| 16.5 | 5.36 | w |
| 16.9 | 5.24 | w |
| 17.4 | 5.09 | m |
| 17.7 | 5.00 | s |
| 18.1 | 4.91 | s |
| 18.7 | 4.75 | m |
| 19.9 | 4.46 | w |
| 20.2 | 4.40 | w |
| 20.5 | 4.34 | w |
| 20.7 | 4.28 | m |
| 21.2 | 4.19 | s |
| 21.7 | 4.09 | w |
| 22.3 | 3.98 | m |
| 22.9 | 3.88 | m |
| 23.2 | 3.84 | w |
| 23.3 | 3.81 | w |
| 23.7 | 3.75 | w |
| 24.0 | 3.70 | w |
| 24.5 | 3.64 | s |
| 24.9 | 3.57 | m |
| 25.4 | 3.51 | m |
| 25.8 | 3.46 | m |
| 26.2 | 3.40 | w |
| 26.7 | 3.34 | w |
| 27.2 | 3.28 | w |
| 27.4 | 3.25 | w |
| 27.9 | 3.20 | w |
| 28.1 | 3.17 | w |
| 28.9 | 3.08 | w |
| 29.3 | 3.04 | w |
| 29.7 | 3.01 | w |

Vs = very strong, s = strong, m = medium, w = weak, and vw = very weak in intensity. It should be noted that intensity values can vary substantially due to preferred orientation effects.

Example 5: Preparation of the Salt of 5-methyl-(6S)-tetrahydrofolic acid and L-isoleucine ethyl ester Form C To 81 mg of amorphous 5-methyl-(6S)-tetrahydrofolic acid L-isoleucine ethyl ester salt, produced by freeze drying of a solution in water-dioxane 4:1, were added 1.0 ml ethanol-water 2:1 (volume ratio) and the mixture was stirred at r.t. for two days. Then the suspension was filtered and the solid submitted to powder X-ray diffraction. Powder X-ray diffraction showed that a crystalline form, designated as Form C was obtained. $^1$H-NMR spectroscopic analysis showed that the molar ratio of 5-methyl-(6S)-tetrahydrofolic acid to L-isoleucine ethyl ester was about 2.8:1

TABLE 3

2-theta angles, d-spacings and qualitative intensities for Form C.

| angle °2Θ | d-spacing [Å] | qualitative intensity |
|---|---|---|
| 5.3 | 16.6 | m |
| 7.0 | 12.6 | vs |

TABLE 3-continued 2-theta angles, d-spacings and qualitative intensities for Form C.

| angle °2Θ | d-spacing [Å] | qualitative intensity |
|---|---|---|
| 8.4 | 10.5 | m |
| 8.8 | 10.1 | s |
| 10.3 | 8.6 | s |
| 10.7 | 8.3 | w |
| 11.2 | 7.9 | s |
| 12.2 | 7.2 | m |
| 13.0 | 6.8 | s |
| 13.3 | 6.7 | m |
| 13.6 | 6.5 | m |
| 14.0 | 6.3 | s |
| 14.7 | 6.00 | m |
| 15.1 | 5.88 | s |
| 15.9 | 5.57 | s |
| 16.8 | 5.28 | s |
| 17.4 | 5.10 | s |
| 17.6 | 5.02 | vs |
| 18.1 | 4.91 | m |
| 18.7 | 4.75 | m |
| 19.0 | 4.68 | w |
| 19.5 | 4.54 | m |
| 20.2 | 4.39 | vs |
| 20.5 | 4.34 | m |
| 20.8 | 4.27 | s |
| 21.2 | 4.19 | m |
| 21.4 | 4.14 | s |
| 22.3 | 3.98 | m |
| 22.6 | 3.94 | m |
| 22.9 | 3.87 | m |
| 23.4 | 3.80 | vs |
| 23.7 | 3.74 | w |
| 24.1 | 3.69 | w |
| 24.5 | 3.63 | s |
| 25.0 | 3.56 | m |
| 25.4 | 3.51 | m |
| 25.8 | 3.45 | m |
| 26.2 | 3.40 | m |
| 26.7 | 3.34 | m |
| 26.9 | 3.31 | s |
| 27.3 | 3.26 | m |
| 28.0 | 3.18 | w |
| 28.5 | 3.13 | w |
| 29.0 | 3.08 | w |
| 29.2 | 3.05 | m |
| 30.4 | 2.93 | w |
| 30.9 | 2.90 | m |

Vs = very strong, s = strong, m = medium, w = weak, and vw = very weak in intensity. It should be noted that intensity values can vary substantially due to preferred orientation effects.

Example 6: Preparation of the Salt of 5-methyl-(6S)-tetrahydrofolic acid and L-isoleucine ethyl ester Out of In Situ Formed 5-Methyl-(6S)-tetrahydrofolic acid from (6S)-tetrahydrofolic acid benzenesulfonate To a mixture of 20 g of [6S]-tetrahydrofolic acid benzenesulfonate (prepared according to EP 0 495 204, assay tetrahydrofolic acid: 72.2% w/w, (6S)-diastereoisomer: 95.9%) and 50 g water were added at 20-30° C. 9.9 mL of an aqueous solution of sodium hydroxide (30% w/w sodium hydroxide) while stirring. Then 0.83 mL of an 1 molar aqueous solution of sodium hydroxide were added and the mixture was cooled to 0-5° C. At 0-5° C. 3.13 mL of an aqueous solution of formaldehyde (concentration: 36.9% w/w) were added and after stirring for 1 hour 0.31 mL of an aqueous solution of sodium hydroxide (30% w/w sodium hydroxide) were added followed by a mixture of 14 g water, 1.7 g of an aqueous solution of sodium hydroxide (30% w/w sodium hydroxide) and 3.07 g sodium borohydride. The mixture was heated to about 63° C. and stirred for 90 minutes. After cooling to ambient temperature 7.9 mL of aqueous hydrochloric acid (37% w/w) were added followed by addition of 4.1 mL of an aqueous solution of sodium hydroxide (30% w/w sodium hydroxide). A small amount of sodium tetraborate was added and the mixture was cooled to 0-5° C. and stirred for about 22 hours. The solids were removed by filtration (suction) and washed with 5 g of water. To the filtrate was added a mixture of 15.86 g of L-isoleucine ethyl ester hydrochloride and 30 g water at ambient temperature while stirring. The mixture was heated to about 66° C. and a small amount of crystalline 5-methyl-(6S)-tetrahydrofolic acid L-isoleucine ethyl ester salt Form A was added for seeding. At about 66° C. 27.1 mL of an 1 molar aqueous solution of hydrochloric acid were added. A suspension was formed. Within about 90 minutes the mixture was cooled to about 20° C. while further 33.2 mL of an 1 molar aqueous solution of hydrochloric acid were added. The crystallized product was isolated by filtration (suction) and washed with 84 mL of water that was pre-cooled in an ice bath. The product was dried for about 60 hours at room temperature in vacuum (10 mbar) to give 17.2 grams of crystalline salt of 5-methyl-(6S)-tetrahydrofolic acid and L-isoleucine ethyl ester Form A (assay 5-methyl-(6S)-tetrahydrofolic acid: 74.0% w/w, purity: 98.6% area, (6S)-diastereoisomer: 99.5%) corresponding to 88.1% assay corrected chemical yield.

Example 7: Preparation of the Salt of 5-methyl-(6S)-tetrahydrofolic acid and L-isoleucine ethyl ester To 1670 g of water were added 250 g of 5-methyl-(6S)-tetrahydrofolic acid (assay: 96.2% w/w) and 256.1 g L-isoleucine ethyl ester hydrochloride at ambient temperature while stirring. 500 g water were added and the pH was adjusted to pH=7.3 by addition of 134.6 mL of an aqueous sodium hydroxide solution (30% w/w sodium hydroxide). The mixture was heated to approximately 66° C. while stirring and a small amount of the salt of 5-methyl-(6S)-tetrahydrofolic acid and L-isoleucine ethyl ester salt Form A was added for seeding. At 66° C. 385 mL of an aqueous 1 molar solution of hydrochloric acid was added within about 30 minutes. Within about 90 minutes the mixture was cooled to about 20° C. while further 365 mL of an aqueous 1 molar solution of hydrochloric acid were added. The crystallized product was isolated by filtration (suction) and washed with 733 g of water that was pre-cooled in an ice bath. The product was dried for about 60 hours at about 40° C. in vacuum (10 mbar) to give 300.8 grams of crystalline salt of 5-methyl-(6S)-tetrahydrofolic acid and L-isoleucine ethyl ester Form A (assay 5-methyl-(6S)-tetrahydrofolic acid: 74.3% w/w, purity: 98.7% area) corresponding to 92.9% assay corrected chemical yield.

Example 8: Preparation of the Salt of 5-methyl-(6S)-tetrahydrofolic acid and L-isoleucine ethyl ester To 250.5 kg of water in a reaction vessel were added 31.0 kg of 5-methyl-(6S)-tetrahydrofolic acid (assay: 96.8% w/w, 6S-diastereoisomer: 98.3%) and 32.0 kg L-isoleucine ethyl ester hydrochloride at ambient temperature while stirring. 16.5 kg water were added and the pH was adjusted to pH=7.3 by addition of 18.6 kg aqueous sodium hydroxide solution (30% w/w sodium hydroxide). The mixture was heated to approximately 66° C. while stirring and solids were removed by filtration. The filter was washed with 20.3 kg water via the reaction vessel. The filtrate and washing were combined in a crystallization vessel and heated to approximately 65° C. 37.5 grams of 5-methyl-(6S)-tetrahydrofolic acid and L-isoleucine ethyl ester Form A were added for seeding. 64.5 kg of aqueous 1 M hydrochloric acid were added at approximately 65° C. within 30 minutes. The mixture was cooled to 20° C. within 90 minutes and the pH was adjusted to pH=5.4 by addition of 1.5 kg of aqueous 1 M hydrochloric acid. The mixture was stirred for 1 hour at approximately 20° C. and the crystallized product was isolated by centrifugation. The product was washed with 45 kg of water that was pre-cooled to approximately 3° C. The product was then dried for 17 hours at 50° C. in vacuum to give 23.63 kg 5-methyl-(6S)-tetrahydrofolic acid L-isoleucine ethyl ester Form A (assay 5-methyltetrahydrofolic acid 77.2% w/w, 6S-diastereoisomer: 99.5%) corresponding to an assay corrected yield of 60.8%. The yield of this example is not representative since part of the crystallized product was lost during centrifugation due to a technical defect.

Example 9: Hygroscopicity and Water Content (DVS Experiments)

The water content of a sample of 5-methyl-(6S)-tetrahydrofolic acid calcium salt was measured and the water content was found to be 12.4%. TG-FTIR analysis of a sample of 5-methyl-(6S)-tetrahydrofolic acid L-isoleucine ethyl ester salt Form A prepared according to example 1 or 2 showed that the sample is essentially free of water.

A sample of 5-methyl-(6S)-tetrahydrofolic acid calcium salt and a sample of 5-methyl-(6S)-tetrahydrofolic acid L-isoleucine ethyl ester salt Form A prepared according to example 1 or 2 (about 20 mg each) were examined by dynamic water vapor sorption analysis (DVS) within the relative humidity range from 0 to 75% r.h. DVS measurements were performed with an SPS11-100n "Sorptions Prüfsystem" from ProUmid (formerly "Projekt Messtechnik"), August-Nagel-Str. 23, 89079 Ulm (Germany). Measurements were conducted as follows: The sample was placed on an aluminum or platinum holder on top of a microbalance and allowed to equilibrate at 50% RH before starting the pre-defined humidity programs:

(1) five hours at 50% relative humidity (RH) then
(2) scan to 50→0% RH at a rate of 5% per hour
(3) maintain constant RH at 0% for five hours
(4) raise RH to 75% at a rate of 5% per hour
(5) maintain constant RH at 75% for five hours
(6) scan to 50% RH at a rate of 5% per hour Comparing the result for 5-methyl-(6S)-tetrahydrofolic acid L-isoleucine ethyl ester salt Form A with the result for the calcium salt shows that the water content of 5-methyl-(6S)-tetrahydrofolic acid L-isoleucine ethyl ester salt Form A changes less than 0.8% within the tested range while the water content for the calcium salt of 5-methyl-(6S)-tetrahydrofolic acid changes by more than 6%. The results are visually illustrated in FIG. 5.

Example 10: Stability of the Salt of 5-methyl-(6S)-tetrahydrofolic acid and L-isoleucine Ethyl Ester In order to compare the long-term stabilities of the salt of 5-methyl-(6S)-tetrahydrofolic acid and L-isoleucine ethyl ester, the compounds of the invention, to the long-term stability of the crystalline calcium salt of 5-methyl-(6S)-tetrahydrofolic acid as prepared according to EP 1 044 975 B1, respective stability data has been generated at various temperatures and humidities.

(a) Stability of the Salt of 5-methyl-(6S)-Tetrahydrofolic acid and L-isoleucine Ethyl Ester at 25° C./60% Rh Crystalline calcium salt of 5-methyl-(6S)-tetrahydrofolic acid, prepared according to literature procedures (EP 1 044 975 B1) and the salt of 5-methyl-(6S)-tetrahydrofolic acid and L-isoleucine ethyl ester Form A were stored at 25° C./60% rh. The content of 5-methyl-(6S)-tetrahydrofolic acid remaining in the samples was measured by HPLC at periodic intervals. The results are shown in Table 4a and FIG. 6. The content of 5-methyl-(6S)-tetrahydrofolic acid remaining was also compared to the initial value at the time of preparation (% rel.). The results are shown in Tables 4b. Additionally the content of the pyrazino-s-triazine derivative of 4α-hydroxy-5-methyl-THF (MeFox), a major degradation product, was measured by HPLC at periodic intervals and disclosed as absolute values (% w/w). The results are shown in Table 5 and FIG. 7.

TABLE 4a

Long-term stability of the salt of 5-methyl-(6S)-tetrahydrofolic acid and L-isoleucine ethyl ester at 25° C./60% rh (% w/w)

| | 5-methyl-(6S)-tetrahydrofolic acid (% w/w) | | | | |
|---|---|---|---|---|---|
| | 0 months | 3 months | 6 months | 9 months | 12 months |
| salt of 5-methyl-(6S)-tetrahydrofolic acid and L-isoleucine ethyl ester | 75.1 | 72.8 | 73.8 | 74.3 | 74.1 |
| crystalline calcium salt of 5-methyl-(6S)-tetrahydrofolic acid | 82.4 | 82.5 | 80.8 | 80.6 | n/a |

TABLE 4b

Long-term stability of the salt of 5-methyl-(6S)-tetrahydrofolic acid and L-isoleucine ethyl ester at 25° C./60% rh (% rel.)

| | 5-methyl-(6S)-tetrahydrofolic acid (% rel.) | | | | |
|---|---|---|---|---|---|
| | 0 months | 3 months | 6 months | 9 months | 12 months |
| salt of 5-methyl-(6S)-tetrahydrofolic acid and L-isoleucine ethyl ester | 100.0 | 97.0 | 98.3 | 98.9 | 98.7 |
| crystalline calcium salt of 5-methyl-(6S)-tetrahydrofolic acid | 100.0 | 100.1 | 98.1 | 97.9 | n/a |

TABLE 5

Long-term stability of the salt of 5-methyl-(6S)-tetrahydrofolic acid and L-isoleucine ethyl ester at 25° C./60% rh (major degradation product [MeFox])

| | Pyrazino-s-triazine derivative of 4α-hydroxy-5-methyl-THF (MeFox) (% w/w) | | | | |
|---|---|---|---|---|---|
| | 0 months | 3 months | 6 months | 9 months | 12 months |
| salt of 5-methyl-(6S)-tetrahydrofolic acid and L-isoleucine ethyl ester | 0.01 | 0.03 | 0.02 | 0.03 | 0.03 |
| crystalline calcium salt of 5-methyl-(6S)-tetrahydrofolic acid | 0.20 | 0.59 | 0.71 | 0.68 | n/a |

(b) Stability of the salt of 5-methyl-(6S)-tetrahydrofolic acid and L-isoleucine Ethyl Ester at 40° C./75% rh Crystalline calcium salt of 5-methyl-(6S)-tetrahydrofolic acid, prepared according to literature procedures (EP 1 044 975 B1) and the salt of 5-methyl-(6S)-tetrahydrofolic acid and L-isoleucine ethyl ester Form A were stored at 40° C./75% rh. The content of 5-methyl-(6S)-tetrahydrofolic acid remaining in the sample was measured by HPLC at periodic intervals. The results are shown in Table 6a and FIG. 8. The content of 5-methyl-(6S)-tetrahydrofolic acid remaining was also compared to the initial value at the time of preparation (% rel.). The results are shown in Tables 6b. Additionally the content of the pyrazino-s-triazine derivative of 4α-hydroxy-5-methyl-THF (MeFox), a major degradation product, was measured by HPLC at periodic intervals and disclosed as absolute values (% w/w). The results are shown in Table 7 and FIG. 9.

TABLE 6a

Long-term stability of the salt of 5-methyl-(6S)-tetrahydrofolic acid and L-isoleucine ethyl ester at 40° C./75% rh (% w/w)

| | 5-methyl-(6S)-tetrahydrofolic acid (% w/w) | | | | |
|---|---|---|---|---|---|
| | 0 months | 3 months | 6 months | 9 months | 12 months |
| salt of 5-methyl-(6S)-tetrahydrofolic acid and L-isoleucine ethyl ester | 75.1 | 72.7 | 73.4 | 73.0 | 74.7 |
| crystalline calcium salt of 5-methyl-(6S)-tetrahydrofolic acid | 82.4 | 81.3 | 80.5 | 81.2 | n/a |

TABLE 6b

Long-term stability of the salt of 5-methyl-(6S)-tetrahydrofolic acid and L-isoleucine ethyl ester at 40° C./75% rh (% rel.)

| | 5-methyl-(6S)-tetrahydrofolic acid (% rel.) | | | | |
|---|---|---|---|---|---|
| | 0 months | 3 months | 6 months | 9 months | 12 months |
| salt of 5-methyl-(6S)-tetrahydrofolic acid and L-isoleucine ethyl ester | 100.0 | 96.8 | 97.8 | 97.2 | 99.5 |
| crystalline calcium salt of 5-methyl-(6S)-tetrahydrofolic acid | 100.0 | 98.7 | 97.6 | 98.5 | n/a |

TABLE 7

Long-term stability of the crystalline monosodium salt of 5-methyl-(6S)-tetrahydrofolic acid at 40° C./75% rh (major degradation product [MeFox])

| | Pyrazino-s-triazine derivative of 4α-hydroxy-5-methyl-THF (MeFox) (% abs.) | | | | |
|---|---|---|---|---|---|
| | 0 months | 3 months | 6 months | 9 months | 12 months |
| salt of 5-methyl-(6S)-tetrahydrofolic acid and L-isoleucine ethyl ester | 0.01 | 0.03 | 0.03 | 0.04 | 0.06 |
| crystalline calcium salt of 5-methyl-(6S)-tetrahydrofolic acid | 0.20 | 0.72 | 0.80 | 0.68 | n/a |

Tables 4 to 7 with the stability data of the salt of 5-methyl-(6S)-tetrahydrofolic acid and L-isoleucine ethyl ester as disclosed in in the present invention clearly are showing that
  i) there is a remarkable difference in the stability of the salt of 5-methyl-(6S)-tetrahydrofolic acid and L-isoleucine ethyl ester compared to the crystalline calcium salt of 5-methyl-(6S)-tetrahydrofolic acid and
  ii) the salt of 5-methyl-(6S)-tetrahydrofolic acid and L-isoleucine ethyl ester is much more stable over a long period of time than crystalline calcium salt of 5-methyl-(6S)-tetrahydrofolic acid.

Example 11: Isomeric Enrichment of the Salts of 5-methyl-(6S)-tetrahydrofolic acid and L-isoleucine Ethyl Ester When preparing salts of 5-methyl-(6S)-tetrahydrofolic acid and L-isoleucine ethyl ester starting with 5-methyl-(6S)-tetrahydrofolic acid the following isomeric enrichment can be obtained (measured by HPLC)

| Experiment no | (6S) content of the starting material (5-methyl-(6S)-tetrahydrofolic acid) [%] | (6S) content of the resulting salt of 5-methyl-(6S)-tetrahydrofolic acid and L-isoleucine ethyl ester [%] |
|---|---|---|
| 1 | 98.0 | 99.6 |
| 2 | 98.0 | 99.7 |
| 3 | 98.0 | 99.7 |
| 4 | 98.0 | 99.6 |
| 5 | 98.0 | 99.6 |

-continued

| Experiment no | (6S) content of the starting material (5-methyl-(6S)-tetrahydrofolic acid) [%] | (6S) content of the resulting salt of 5-methyl-(6S)-tetrahydrofolic acid and L-isoleucine ethyl ester [%] |
|---|---|---|
| 6 | 98.0 | 99.6 |
| 7 | 98.0 | 99.7 |

When preparing salts of 5-methyl-(6S)-tetrahydrofolic acid and L-isoleucine ethyl ester starting with in situ prepared 5-methyl-(6S)-tetrahydrofolic acid benzenesulfonate the following isomeric enrichment can be obtained (measured by HPLC)

| Experiment no | (6S) content of the starting material ((6S)-tetrahydrofolic acid benzenesulfonate) [%] | (6S) content of the resulting salt of 5-methyl-(6S)-tetrahydrofolic acid and L-isoleucine ethyl ester [%] |
|---|---|---|
| 8 | 95.9 | 99.5 |

The invention claimed is:

1. A crystalline salt of 5-methyl-(6S)-tetrahydrofolic acid and L-isoleucine ethyl ester wherein the molar ratio of 5-methyl-(6S)-tetrahydrofolic acid to L-isoleucine ethyl ester is from 1:0.3 to 1:2.0 (in mol/mol) and/or hydrates and/or solvates thereof.

2. The crystalline salt of claim 1, wherein the molar ratio of 5-methyl-(6S)-tetrahydrofolic acid to L-isoleucine ethyl ester is from 1:0.5 to 1:1.5 (in mol/mol) and/or hydrates and/or solvates thereof.

3. The crystalline salt according to claim 1, wherein the ratio of 5-methyl-(6S)-tetrahydrofolic acid to L-isoleucine ethyl ester is approximately 1:1 (in mol/mol) and/or hydrates and/or solvates thereof.

4. The crystalline salt according to claim 1, wherein the salt is the salt of 5-methyl-(6S)-tetrahydrofolic acid and L-isoleucine ethyl ester and has a PXRD pattern with at least one characteristic peak (expressed in 2θ±0.2° 2θ (CuKα radiation)) selected from the following peaks located at 5.8, 6.9, 14.0, 17.5, and 22.2 (Form A).

5. The crystalline salt according to claim 1 wherein the salt of 5-methyl-(6S)-tetrahydrofolic acid and L-isoleucine ethyl ester has a PXRD pattern as shown in FIG. 1 (Form A).

6. The crystalline salt according to claim 1 wherein the salt is the salt of 5-methyl-(6S)-tetrahydrofolic acid and L-isoleucine ethyl ester and has a Raman spectrum—with at least one characteristic peak (expressed in wavenumbers, $cm^{-1\pm2}$ $cm^{-1}$) selected from the following peaks located at 1607, 1571, 1506, 1250, and 650 (Form A).

7. The crystalline salt according to claim 1, wherein the salt of 5-methyl-(6S)-tetrahydrofolic acid and L-isoleucine ethyl ester has a Raman spectrum substantially as shown in FIG. 4 (Form A).

8. The crystalline salt according to claim 1, wherein the salt is the salt of 5-methyl-(6S)-tetrahydrofolic acid and L-isoleucine ethyl ester and has a PXRD pattern with at least one characteristic peak (expressed in 2θ±0.2° 2θ (CuKα radiation)) selected from the following peaks located at 5.3, 7.0, 14.0, 17.7, and 24.5 (Form B).

9. The crystalline salt according to claim 1, wherein the salt is the salt of 5-methyl-(6S)-tetrahydrofolic acid and L-isoleucine ethyl ester and has a PXRD pattern with at least three characteristic peaks (expressed in 2θ+0.2° 2θ (CuKα radiation)) selected from the following peaks located at 5.3, 7.0, 14.0, 17.7, and 24.5 (Form B).

10. The crystalline salt according to claim 1, wherein the salt is the salt of 5-methyl-(6S)-tetrahydrofolic acid and L-isoleucine ethyl ester and has a PXRD pattern as shown in FIG. 2 (Form B).

11. The crystalline salt according to claim 1, wherein the salt is the salt of 5-methyl-(6S)-tetrahydrofolic acid and L-isoleucine ethyl ester and has a PXRD pattern with at least one characteristic peak (expressed in 2θ±0.2° 2θ (CuKα radiation)) selected from the following peaks located at 7.0, 8.8, 14.0, 17.6, 20.2, 23.4, and 26.9 (Form C).

12. The crystalline salt according to claim 1, wherein the salt is the salt of 5-methyl-(6S)-tetrahydrofolic acid and L-isoleucine ethyl ester and has a PXRD pattern with at least three characteristic peaks (expressed in 2θ±0.2° 2θ (CuKα radiation)) selected from the following peaks located at 7.0, 8.8, 14.0, 17.6, 20.2, 23.4, and 26.9 (Form C).

13. The crystalline salt according to claim 1, wherein the salt is the salt of 5-methyl-(6S)-tetrahydrofolic acid and L-isoleucine ethyl ester and has a PXRD pattern as shown in FIG. 3 (Form C).

14. The crystalline salt according to claim 1 having at least 99% or more chemical, stereoisomerical and crystalline purity.

15. A process for obtaining the crystalline salt of 5-methyl-(6S)-tetrahydrofolic acid and L-isoleucine ethyl ester according to claim 1 comprising the steps of:
    i) preparing a mixture of 5-methyl-(6S)-tetrahydrofolic acid in water and adding L-isoleucine ethyl ester, optionally in a solvent or a mixture of solvents;
    ii) adding a base, optionally in a solvent or a mixture of solvents, to achieve dissolution;
    iii) heating the composition to at least 60° C.;
    iv) adding an acid to adjust the pH to the range from 4 to 7;
    v) crystallizing and cooling the mixture to a temperature between 1° C. and 30° C., optionally stirring the obtained suspension at the end temperature; and
    vi) isolating the obtained solid material and optionally drying the resultant product.

16. The process of claim 15, wherein the molar ratio of 5-methyl-(6S)-tetrahydrofolic acid and L-isoleucine ethyl ester hydrochloride in step ii) is in the range of from 1:1 to 1:3; and/or
    in step i) the mixture of 5-methyl-(6S)-tetrahydrofolic acid in water is prepared in situ; and/or
    in step i) L-isoleucine ethyl ester is used in form of its hydrochloride salt; and/or
    in step ii) aqueous sodium hydroxide solution is used to dissolve the compounds and that in step iv) aqueous hydrochloric acid is used for the pH adjustment; and/or
    in step ii) the pH after the addition of the base is in the range of from 6.5 to 9.0; and/or
    in step iii) charcoal is added and then the solution is clear filtrated; and/or
    the solvent is water; and/or
    in step iv) the pH value achieved by addition of the acid set to be in the range of 5.4 to 6.4; and/or
    in step iii), iv) and/or v) seed crystals are added.

17. A pharmaceutical composition, food additive and/or preparation comprising the crystalline salt of 5-methyl-(6S)-tetrahydrofolic acid and L-isoleucine ethyl ester according to claim 1 and optionally one or more acceptable excipients.

18. A method for treatment in homocysteine-lowering, anemia, neural tube defects, cardiovascular diseases, depression, cognitive impairment, Alzheimer's disease, osteoporosis, dietary management of low plasma and/or low red blood cell folate and/or low cerebrospinal fluid folate and/or low peripheral or central nervous system folate, comprising administering to a subject in need thereof an effective amount of the crystalline salt of 5-methyl-(6S)-tetrahydrofolic acid and L-isoleucine ethyl ester according to claim 1.

19. A crystalline salt of 5-methyl-(6S)-tetrahydrofolic acid and L-isoleucine ethyl ester wherein the molar ratio of 5-methyl-(6S)-tetrahydrofolic acid to L-isoleucine ethyl ester is from 1:0.3 to 1:2.0 (in mol/mol).

20. The crystalline salt according to claim 1, wherein the ratio of 5-methyl-(6S)-tetrahydrofolic acid to L-isoleucine ethyl ester is 1:1 (in mol/mol).

21. The crystalline salt of claim 1, wherein the molar ratio of 5-methyl-(6S)-tetrahydrofolic acid to L-isoleucine ethyl ester is from 1:0.75 to 1:1.5(in mol/mol) and/or hydrates and/or solvates thereof.

22. The crystalline salt according to claim 1, wherein the salt is the salt of 5-methyl-(6S)-tetrahydrofolic acid and L-isoleucine ethyl ester and has a PXRD pattern with at least three characteristic peaks (expressed in 2θ±0.2° 2θ (CuKα radiation)) selected from the following peaks located at 5.8, 6.9, 14.0, 17.5,and 22.2 (Form A).

23. The crystalline salt according to claim 1, wherein the salt is the salt of 5-methyl-(6S)-tetrahydrofolic acid and L-isoleucine ethyl ester and has a PXRD pattern with at least one characteristic peak (expressed in 2θ±0.2° 2θ (CuKα radiation)) selected from the following peaks located at 5.8, 6.9, 8.5, 12.5, 12.9, 14.0, 14.9, 16.2, 17.5, 17.9, 18.9, 19.2, 22.2, 24.4, 25.4 25.8, 25.9, and 34.6(Form A).

24. The crystalline salt according to claim 1, wherein the salt is the salt of 5-methyl-(6S)-tetrahydrofolic acid and L-isoleucine ethyl ester and has a Raman spectrum-with at least one characteristic peak (expressed in wavenumbers, $cm^{-1}±2\ cm^{-1}$) selected from the following peaks located at 2961, 2938, 1607, 1571, 1506, 1468, 1332, 1250, 1153, 922, 860, and 650 (Form A).

25. The crystalline salt according to claim 1, wherein the salt is the salt of 5-methyl-(6S)-tetrahydrofolic acid and L-isoleucine ethyl ester and has a PXRD pattern with at least one characteristic peak (expressed in 2θ±0.2° 2θ (CuKα radiation)) selected from the following peaks located at 5.3, 7.0, 8.4, 13.0, 13.2, 14.0, 14.7, 15.9, 17.4, 17.7, 18.1, 18.7, 20.7, 21.2, 22.9, 24.5, and 25.4 (Form B).

26. The crystalline salt according to claim 1, wherein the salt is the salt of 5-methyl-(6S)-tetrahydrofolic acid and L-isoleucine ethyl ester and has a PXRD pattern with at least one characteristic peak (expressed in 2θ±0.2° 2θ (CuKα radiation)) selected from the following peaks located at 5.3, 7.0, 8.8, 11.2, 13.0, 14.0, 15.1, 15.9, 16.8, 17.4, 17.6, 20.2, 20.5, 20.8, 21.2, 21.4, 23.4, 24.5, 26.9,and 32.2 (Form C).

* * * * *